United States Patent
Zieger et al.

(10) Patent No.: US 11,071,453 B2
(45) Date of Patent: Jul. 27, 2021

(54) SYSTEMS AND METHODS FOR REFLECTION-BASED POSITIONING RELATIVE TO AN EYE

(71) Applicant: ALCON INC., Fribourg (CH)

(72) Inventors: Peter Zieger, Berlin (DE); Martin Gruendig, Rangsdorf (DE); Sascha Birkner, Berlin (DE)

(73) Assignee: Alcon Inc., Fribourg (CH)

( * ) Notice: Subject to any disclaimer, the term of this patent is extended or adjusted under 35 U.S.C. 154(b) by 159 days.

(21) Appl. No.: 16/428,492

(22) Filed: May 31, 2019

(65) Prior Publication Data

US 2019/0374102 A1 Dec. 12, 2019

Related U.S. Application Data

(60) Provisional application No. 62/681,440, filed on Jun. 6, 2018.

(51) Int. Cl.
*A61B 3/15* (2006.01)
*A61B 3/00* (2006.01)

(52) U.S. Cl.
CPC ............ *A61B 3/152* (2013.01); *A61B 3/0008* (2013.01); *A61B 3/0025* (2013.01); *A61B 3/0075* (2013.01)

(58) Field of Classification Search
CPC .......... A61F 2009/0087; A61F 9/00825; A61F 2009/00872; A61F 2009/00897; A61F 2009/00889; A61F 9/008; A61F 2009/00846; A61F 2009/00887; A61F 9/00827; A61F 9/00838; A61F 2009/00844; A61F 9/00804; A61F 9/009; A61F 2009/00842; A61F 2009/00865; A61F 2009/00895; A61F 9/00829; A61F 9/00834; A61B 3/0025; A61B 3/113; A61B 3/0008; A61B 3/0075; A61B 3/152; A61B 1/0607; A61B 1/0638; A61B 1/0669; A61B 1/07; A61B 2090/306;
(Continued)

(56) References Cited

U.S. PATENT DOCUMENTS 5,596,377 A 1/1997 Yano
5,644,375 A 7/1997 Suzuki
(Continued)

FOREIGN PATENT DOCUMENTS

EP 2113192 A1 11/2009
JP 3617708 B2 2/2005
(Continued)

OTHER PUBLICATIONS

US 10,258,234 B2, 04/2019, Sakurada (withdrawn)

*Primary Examiner* — Brandi N Thomas (57) ABSTRACT

Disclosed are systems and methods for aligning an ophthalmic device with respect to an eye of a patient. In one disclosure, the system may include an ophthalmic device with an on-axis and an off-axis. The system may include an on-axis illuminator that emits light that is reflected by the eye of the patient to form an on-axis reflection having a center. The system may include an on-axis camera pointed along the on-axis. The system may include an off-axis illuminator that emits light that is reflected by the eye to form an off-axis reflection having a center. The system may include an off-axis camera pointed along the off-axis. The ophthalmic device may be operable to be aligned with respect to the eye of the patient when the on-axis is substantially normal to the center of the on-axis reflection and the off-axis is substantially normal to the center of the off-axis reflection.

9 Claims, 10 Drawing Sheets

(58) Field of Classification Search
CPC ...... A61B 3/14; A61B 5/0059; A61B 5/0077; A61B 90/20; A61B 90/30; A61B 90/361; A61B 2018/20351; A61B 2018/20361; A61B 2018/204; A61B 2090/061; A61B 2560/0223; A61B 2576/02; A61B 3/0033; A61B 3/0041; A61B 3/024; A61B 3/08; A61B 3/1025; A61B 3/107; A61B 3/1173; A61B 3/12; A61B 3/18; G03H 1/0406; G03H 1/0443; G03H 1/0866; G03H 1/265; G03H 1/28; G03H 2001/0456; G03H 2001/046; G03H 2001/0469; G03H 2226/11; G03H 2226/13; G03H 2001/2655; G03H 2222/13; G03H 2223/16
See application file for complete search history.

(56) References Cited

U.S. PATENT DOCUMENTS

| | | | |
|---|---|---|---|
| 6,082,860 A | 7/2000 | Takagi | |
| 6,132,046 A | 10/2000 | Iijima | |
| 6,257,722 B1 | 7/2001 | Toh | |
| 6,322,216 B1 | 11/2001 | Yee | |
| 8,221,399 B2 | 7/2012 | Amano | |
| 9,408,531 B2 | 8/2016 | Okada | |
| 9,706,920 B2 | 7/2017 | Okada | |
| 10,080,496 B2 | 9/2018 | Tokuda | |
| 10,123,700 B2 | 11/2018 | Nakajima | |
| 2002/0159028 A1 | 10/2002 | Masaki | |
| 2004/0119943 A1 | 6/2004 | Rathjen | |
| 2004/0156019 A1 | 8/2004 | Masaki | |
| 2005/0133693 A1* | 6/2005 | Fouquet | G01J 3/427 250/214 R |
| 2009/0190093 A1 | 7/2009 | Tanassi | |
| 2013/0321771 A1 | 12/2013 | Yuasa | |
| 2015/0085252 A1 | 3/2015 | Fujimura | |
| 2015/0327763 A1 | 11/2015 | Shimizu | |
| 2019/0090736 A1 | 3/2019 | Nakajima | |

FOREIGN PATENT DOCUMENTS

| | | |
|---|---|---|
| JP | 3710571 B2 | 10/2005 |
| JP | 6325856 B2 | 5/2018 |

* cited by examiner

SYSTEMS AND METHODS FOR REFLECTION-BASED POSITIONING RELATIVE TO AN EYE

FIELD OF THE DISCLOSURE

The present disclosure relates to systems and methods for positioning a device, such as a diagnostic or surgical device, with respect to an eye.

BACKGROUND

In ophthalmology, an exact positioning of a device, such as a diagnostic or surgical device, relative to the eye is often crucial for accurate results. It may be important to center part of the device in front of the eye and set part of the device at a precise distance from the eye.

Many techniques may be used to align a device. For example, a reflection-based technique may be used in which individual light sources are reflected on the cornea and imaged with a camera or eye. The size and or position of the reflection is used to position the device.

A height-based technique may also be used. Alignment can be achieved, for example, by using the distance information provided by the Scheimpflug-technique or with the volume information of an optical coherence tomography (OCT) system.

An image-based technique may use the sharpness of the image of the eye to determine the distance as used, for example, in cameras to automatically focus a scene on the sensor.

A stereo-based technique may involve photogrammetric measurement of distance and detecting the same eye features (e.g. pupil, limbus) at different points of reference.

SUMMARY

Disclosed herein are systems for aligning an ophthalmic device with respect to an eye of a patient. The system may include an ophthalmic device. The ophthalmic device may include an on-axis illuminator; an on-axis camera, an off-axis illuminator; and an off-axis camera. The system may include an on-axis and an off-axis that intersects the on-axis, at an acute off-axis angle. The system may be configured such that the on-axis illuminator emits light that is incident on and reflected by the eye of the patient to form an on-axis reflection having a center. The system may be configured such that the on-axis camera is pointed along the on-axis such that the on-axis camera captures an on-axis image including the on-axis reflection and produces on-axis image data representative of the on-axis image, including the on-axis reflection. The system may be configured such that the off-axis illuminator emits light along an off-axis incident path that is incident on and reflected by the eye along an off-axis reflective path to form an off-axis reflection having a center. The system may be configured such that the off-axis camera is pointed along the off-axis such that the off-axis camera captures an off-axis image including the off-axis reflection and produces off-axis image data representative of the off-axis image, including the off-axis reflection. The system may be configured such that the ophthalmic device is operable to be aligned with respect to the eye of the patient when the on-axis is substantially normal to the center of the on-axis reflection and the off-axis is substantially normal to the center of the off-axis reflection.

The system may have the following additional features, which may further be combined with one another in any possible combinations unless clearly mutually exclusive:

The system may be configured such that on-axis camera is enclosed within the on-axis illuminator.

The system may be configured such that the off-axis camera is enclosed within the off-axis illuminator.

The system may be configured such that the on-axis illuminator has a shape with a defined center.

The system may be configured such that the system includes a processor. The processor may be coupled to receive the on-axis image data and the off-axis image data and produce a pass signal when the ophthalmic device is aligned with respect to the eye of the patient.

The system may include an off-axis angle in the range from 0° to 90, or from 15° to 75°. For example, the off-axis angle may be set to 45 degrees.

The system may include a control interface coupled to receive an input from a user and produce a control signal. The system may include a motor coupled to receive the control signal and adjust a position of the ophthalmic device relative to an eye of a patient.

The system may include a processor coupled to receive the on-axis image data and the off-axis image data and send an instruction signal. The system may include a motor coupled to receive the instruction signal and adjust a position of the ophthalmic device relative to the eye.

The system may include a screen coupled to display a processed image. The processed image may include at least a portion of the on-axis image received by the on-axis camera and at least a portion of the off-axis image received by the off-axis camera.

Disclosed herein are methods for aligning an ophthalmic device with an eye of a patient. The method may include placing the ophthalmic device at a position relative to the eye of the patient, the position comprising a x-position, y-position, and z-position. The method may include lighting a first portion of the eye of the patient with an on-axis illuminator, producing an on-axis reflection having a center. The method may include lighting a second portion of the eye of the patient with an off-axis illuminator, producing an off-axis reflection having a center. The method may include receiving with an on-axis camera pointed along an on-axis, an on-axis image including the on-axis reflection. The method may include receiving with an off-axis camera pointed along an off-axis, an off-axis image including the off-axis reflection. The method may include determining whether the on-axis is substantially normal to the center of the on-axis reflection. The method may include determining whether the off-axis is substantially normal to the center of the off-axis reflection. The method may include, when the on-axis is not substantially normal to the center of the on-axis reflection, adjusting at least one of the x-position and y-position of the ophthalmic device. The method may include, when the off-axis is not substantially normal to the center of the off-axis reflection, adjusting the z-position of the ophthalmic device.

The method may have the following additional steps and features, which may further be combined with one another in any possible combinations unless clearly mutually exclusive:

The method may include enclosing the on-axis camera within the on-axis illuminator.

The method may include enclosing the off-axis camera within the off-axis illuminator.

The method may include generating on-axis image data representing the on-axis image. The method may include generating off-axis image data representing the off-axis image. The method may include sending the on-axis image data to a processor. The method may include sending the off-axis image data to the processor. The method may include generating, with the processor, an instruction signal. The method may include sending an instruction signal to a motor.

The method may include displaying on a screen at least a portion of the on-axis image superimposed with at least a portion of the off-axis image.

The method may include generating an on-axis graphical representation of at least a portion of the on-axis image. The method may include generating an off-axis graphical representation of at least a portion of the off-axis image. The method may include displaying on a screen at least a portion of the on-axis graphical representation. The method may include displaying on the screen at least a portion of the off-axis graphical representation.

The method may include setting an allowable margin of error comprising at least one value corresponding to a distance from the on-axis to the center of the on-axis reflection.

Disclosed herein are methods for arranging components of a system for aligning an ophthalmic device with an eye of a patient. The method may include pointing an on-axis camera along an on-axis. The method may include setting an off-axis angle by pointing an off-axis camera along an off-axis, wherein the off-axis intersects the on-axis at an intersection point, the off-axis angle being the acute angle formed by the intersection of the on-axis and the off-axis. The method may include placing an on-axis illuminator at an on-axis position, wherein the on-axis illuminator is operable to emit visible and/or infrared light towards the intersection point. The method may include placing an off-axis illuminator at an off-axis position relative to the on-axis camera and the on-axis illuminator. The placing an off-axis illuminator may be done such that the off-axis illuminator, by being placed at the off-axis position, is operable to emit light towards the intersection point along an off-axis incident path. An apex of an eye, if placed at the intersection point, would reflect light emitted by the off-axis illuminator forming an off-axis reflection with a center, the off-axis substantially centered in the off-axis reflection.

The method may have the following additional steps and features, which may further be combined with one another in any possible combinations unless clearly mutually exclusive:

The method may include enclosing the on-axis camera within the on-axis illuminator.

The method may include enclosing the off-axis camera within the off-axis illuminator.

The method may include setting an allowable margin of error. The margin of error may include a first value corresponding to a distance from the on-axis to the center of the on-axis reflection. The margin of error may include a second value corresponding to a distance from the off-axis to the center of the off-axis reflection.

The above system may be operable to perform the above methods, or may result from the above methods. The above methods may be used with or to result in the above system. In addition, the above methods may be used with one another to result in and operate an ophthalmic device. The above disclosure further includes the use of an ophthalmic device or a system for aligning an ophthalmic device according to the above methods.

BRIEF DESCRIPTION OF THE DRAWINGS

For a more complete understanding of the present disclosure and its features and advantages, reference is now made to the following description, taken in conjunction with the accompanying drawings, which depict various embodiments of the disclosure.

DETAILED DESCRIPTION

In the following description, details are set forth by way of example to facilitate discussion of the disclosed subject matter. It should be apparent to a person of ordinary skill in the field, however, that the disclosed embodiments are exemplary and not exhaustive of all possible embodiments and furthermore than the component features of the disclosed embodiments may be combined with one another unless clearly mutually exclusive, even though every such combination is not expressly described.

As will be described in further detail, the inventors of the present disclosure have developed methods and systems for use in diagnostic applications and ophthalmic surgery. The ophthalmic systems and methods disclosed herein may be used for improved alignment with the eye. Better alignment allows for more accurate diagnosis and surgical procedures.

The systems and methods for alignment disclosed herein may be fast, cost-efficient and simple to implement. The systems and methods may produce information that is very easy to interpret for the user. For example, the user may need only adjust the system to center bright reflections in one or two images (one off- and one on-axis image). Centering the reflections will position the system in a defined x, y and z position relative to the cornea of the eye. The methods and systems allow for accurate alignment despite variations in corneal shape and size because the methods and systems may rely solely on reflections from the apex.

Some figures and descriptions in this disclosure include an x-y-z orientation for reference purposes. The designations of the x, y, and z axes are arbitrary and may be rearranged. An axis labeled as a circle enclosing a point indicates a three-dimensional system, which can be imagined as extending at a normal from the page. In FIGS. 1-4, the y-axis is perpendicular to an on-axis. Adjusting or moving a position of an ophthalmic device or system means moving at least a portion of the device or system.

The systems and methods disclosed herein may be used to align any number of ophthalmic devices. For example, the systems and methods may be used to align any ophthalmic diagnostic device such as a keratometer, any ophthalmic surgical devices such as a laser, lenses, or any other ophthalmic device.

Figure 1A:
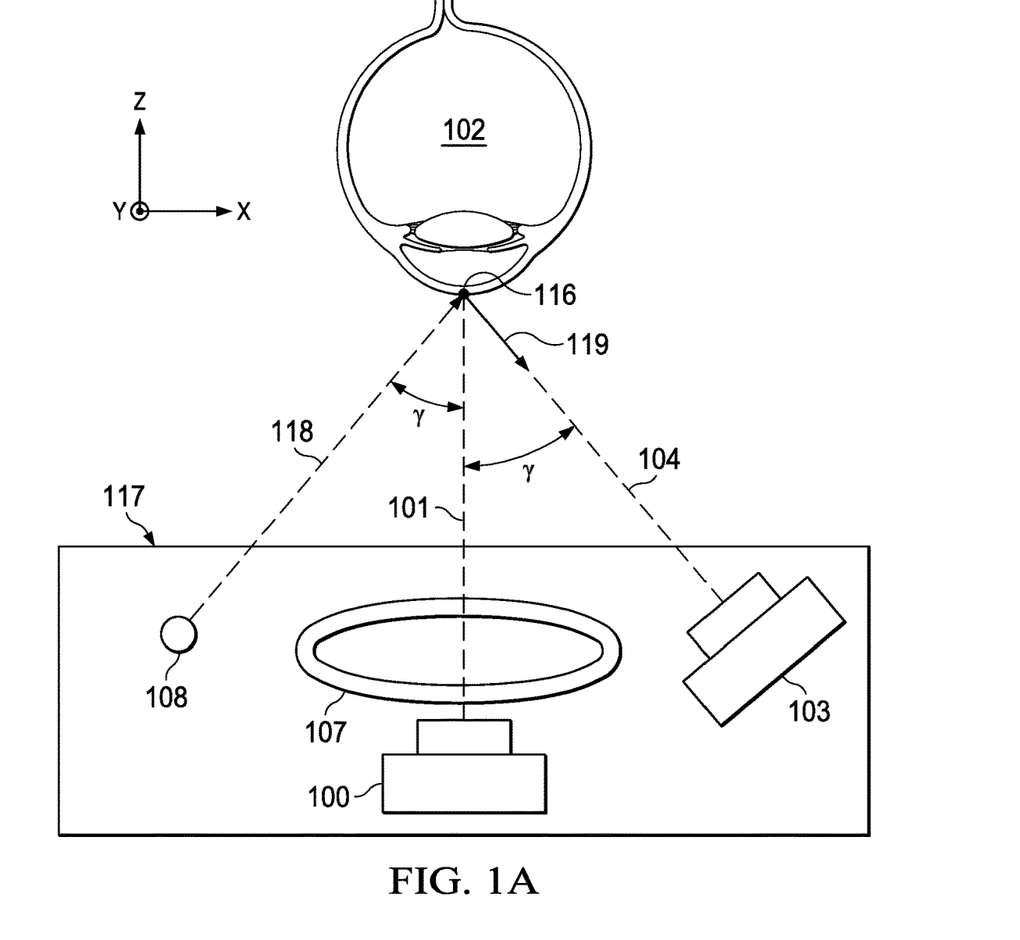
FIG. 1A is a schematic diagram of an ophthalmic system with multiple cameras and illuminators in an aligned position with respect to an eye.

FIG. 1A depicts an ophthalmic system 117 with multiple cameras and illuminators in an aligned position. On-axis camera 100 is pointed toward an eye 102 of a patient along an on-axis 101. The on-axis may be perpendicular to a portion of the eye 102 used to determine the aligned position. For example, the on-axis 101 may be perpendicular to the apex 116 of the cornea or the on-axis 101 may pass through and be parallel to the center of the pupil. Off-axis camera 103 is pointed toward the eye 102 along an off-axis 104. The intersection between the on-axis 101 and the off-axis 104 forms an off-axis angle γ. The off-axis angle γ may be acute (between 0° and 90°, more particularly between 15° and 75°, as illustrated in FIG. 1A. In some embodiments, the off-axis angle γ is 45 degrees, also as illustrated in FIG. 1A.

On-axis camera 100 and Off-axis camera 103 may continuously record images or may capture images at predetermined or user-inputted intervals. Although only two cameras (on-axis camera 100 and off-axis camera 103) are shown in the embodiment in FIG. 1A, additional cameras may be used. In particular, additional off-axis cameras at the same off-axis angle or at different off-axis angles may be used. Off-axis camera 103 is shown as positioned at a distance from on-axis camera 100 in the x-direction, but off-axis camera 103 may also be positioned at the same x-position as on-axis camera 100 and may be instead separated from on-axis camera 100 by, for example, a distance in the y-direction.

On-axis illuminator 107 encloses and encircles on-axis camera 100. On-axis illuminator 107 may include a fixation light, single or multiple light emitting diodes (LEDs), organic light-emitting diodes (OLEDs), liquid-crystal displays (LCDs), plasma displays, or other lighting technology such as projection or conventional light bulbs, or combinations thereof. On-axis illuminator 107, although shown as a circle, may take a variety of shapes for which a center is readily defined, such as a square, rhombus, other regular polygon, or oval, or a dot pattern arranged in such a shape. On-axis camera 100 is pointed along on-axis 101 through on-axis illuminator 107. Although on-axis camera 100 is positioned behind on-axis illuminator 107 in the y-direction in the depicted embodiment, on-axis camera 100 may be positioned at the same y-position as the on-axis illuminator 107 or in front of on-axis illuminator 107. Additionally, on-axis illuminator 107 need not enclose on-axis camera 100. On-axis illuminator 107 may be shaped as a single point, for example, by using one LED, or shaped as two intersecting lines or other shapes. The size and shape of on-axis illuminator 107 may be independent of corneal shape and size.

Off-axis illuminator 108 is positioned away from the off-axis camera 103. Off-axis illuminator 108 and off-axis camera 103 may be placed at the same or different distances from on-axis camera 100. Off-axis illuminator 108 may include a fixation light, single or multiple light emitting diodes (LEDs), organic light-emitting diodes (OLEDs), liquid-crystal displays (LCDs), plasma displays, or other lighting technology such as projection or conventional light bulbs, or combinations thereof. Off-axis illuminator 108, although shown as a point, may take a may take a variety of shapes for which a center is readily defined, such as a square, rhombus, other regular polygon, or oval, or a dot pattern arranged in such a shape. Off-axis illuminator 108 may enclose off-axis camera 103. Off-axis illuminator 108 may be placed at an equal distance from the on-axis 101 as off-axis camera 103.

The ophthalmic system 117 or portions thereof may be aligned in the x- and y-directions as follows. On-axis illuminator 107 may emit light that is incident on the eye 102. Light incident on the eye 102 may be reflected to form an on-axis reflection 112, having a center. The on-axis reflection 112 may reach on-axis camera 100 and off-axis camera 103 The on-axis camera 100 and off-axis camera 103 can capture images of light reflected from the eye 102. The on-axis camera 100 may be pointed along on-axis 101. The off-axis camera 103 may be pointed along off-axis 104. The images may include image data, including digital or analog values that represent the image. A user or computer can use the images to determine whether the ophthalmic system 117 or portions thereof are aligned with the eye 102. When the on-axis 101 is normal to the center of the on-axis reflection 112, the ophthalmic system 117 or portions thereof are aligned in the x- and y-directions.

The ophthalmic system 117 or portions thereof may be aligned in the z-direction as follows. Off-axis illuminator 108 may emit light that travels along off-axis incident path 118 such that the light is incident on the eye 102. Light incident along off-axis incident path 118 may be reflected at the eye 102 along the off-axis reflective path 119 to form an off-axis reflection 113, having a center. In FIG. 1A, the center of the apex 116 of the eye 102 is in the off-axis reflective path 119. The off-axis reflection 113 may reach on-axis camera 100 and off-axis camera 103. The on-axis camera 100 and off-axis camera 103 can capture images of reflected light from the eye 102. The on-axis camera 100 may be pointed along on-axis 101. The off-axis camera 103 may be pointed along off-axis 104. The images may include image data, including digital or analog values that represent the image. A user or processor can use the images to determine whether the ophthalmic system 117 or portions thereof are aligned with the eye 102. When the off-axis 104 is normal to the center of the off-axis reflection 113, as shown, the ophthalmic system 117 or portions thereof are aligned in the z-direction. Off-axis camera 103 may be placed such that the off-axis 104 is normal to the center of the off-axis reflection 113.

Figure 1B:
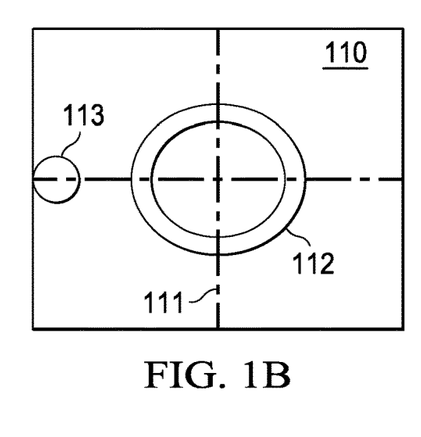
FIG. 1B is a schematic diagram of an on-axis image captured by on-axis camera of the ophthalmic system of FIG. 1A.

FIG. 1B depicts on-axis image 110 received by on-axis camera 100 in ophthalmic system 117 shown in FIG. 1A. On-axis image 110 may be represented by electronic image data, including digital or analog values. On-axis image 110 may be displayed against a grid 111. On-axis image 110 may depict on-axis reflection 112 of the on-axis illuminator 107 from the eye 102. In the image captured at this position of the ophthalmic system 117, on-axis camera 100 is in an aligned position as on-axis reflection 112 is in the center of on-axis image 110. On-axis 101 is normal to the center of the apex 116 of the eye 102 and the on-axis reflection 112. On-axis reflection 112 is also in the center of grid 111. On-axis image 110 may be sent to a processor, displayed on a screen, or both. A user or processor may determine whether the on-axis camera 100 is centered based on the on-axis image 110. Although on-axis reflection 112 is precisely centered in on-axis image 110 in FIG. 1B, a margin of error may be set such that on-axis camera 100 is in an aligned position, even when it is not perfectly centered. Also captured in on-axis image 110, is off-axis reflection 113 of off-axis illuminator 108 off the eye 102 of the patient. A user or processor may also gather information about the relative position of all or part of ophthalmic system 117 based on the position of off-axis reflection 113 in on-axis image 110.

Figure 1C:
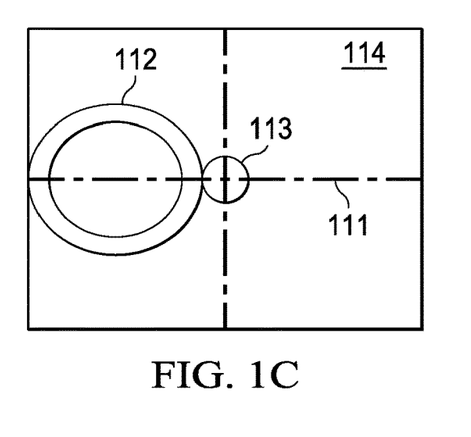
FIG. 1C is a schematic diagram of an off-axis image captured by the off-axis camera of ophthalmic system of FIG. 1A.

FIG. 1C depicts an off-axis image 114 received by the off-axis camera 103 in ophthalmic system 117 of FIG. 1A. Off-axis image 114 may be represented by electronic image data, including digital or analog values. Off-axis image 114 may be displayed against a grid 115. Off-axis image 114 may depict off-axis reflection 113 of off-axis illuminator 108 from the eye 102. The off-axis camera 103 is in an aligned position as shown by the position of the off-axis reflection 113 in the center of the off-axis image 114. Off-axis 104 is normal to the center of the apex 116 of the eye 102 at off-axis angle γ. Off-axis 104 is normal to the center of off-axis reflection 113. The off-axis reflection 113 is also in the center of grid 115. Off-axis image 114 may be sent to a processor, displayed on a screen, or both. A user or processor may determine whether off-axis camera 103 is centered based on off-axis image 114. Although off-axis reflection 113 is precisely centered in off-axis image 114 in FIG. 1C, a margin of error may be set such that off-axis camera 103 is in an aligned position, even when it is not perfectly centered. Also captured in off-axis image 114 is on-axis reflection 112 of on-axis illuminator 107 off the eye 102 of the patient. A user or processor may also gather information about the relative position of all or part of the ophthalmic system 117 based on the position of on-axis reflection 112 in off-axis image 114.

Figure 2A:
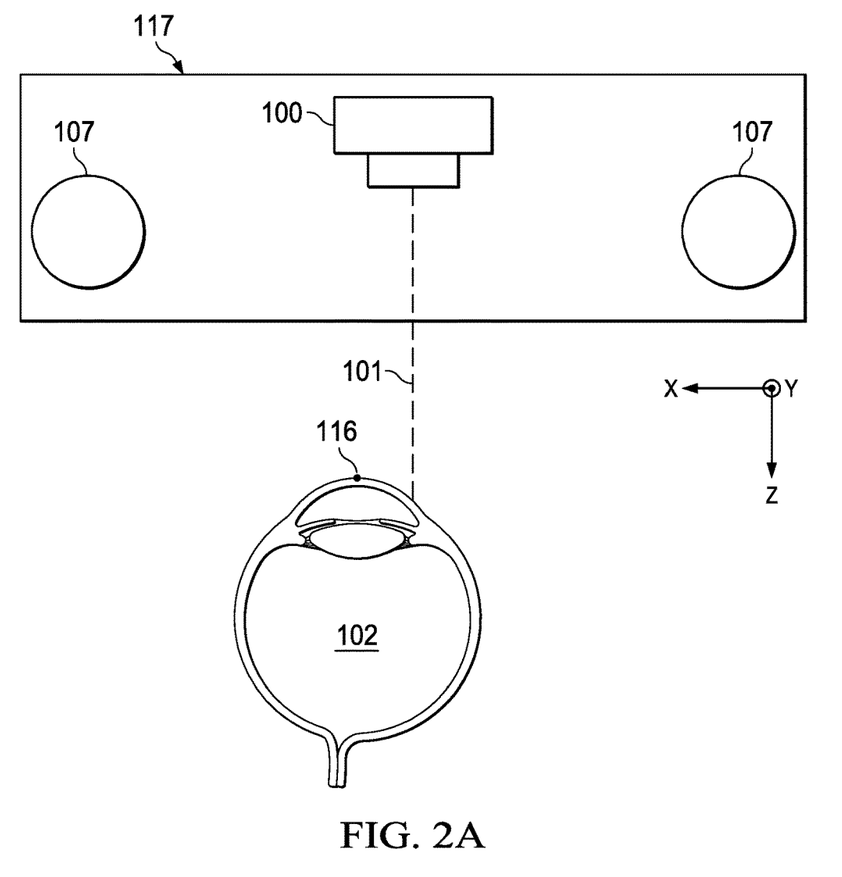
FIG. 2A is a schematic diagram of an ophthalmic system with an on-axis camera and illuminator when the camera is not in an aligned position.

FIG. 2A depicts ophthalmic system 117 with an on-axis camera 100 and on-axis illuminator 107 when the on-axis camera 100 is not in an aligned position with respect to an eye 102. On-axis camera 100 is pointed along on-axis 101 generally towards the eye 102. On-axis 101 is not normal to the center of the apex 116 of an eye 102. On-axis 101 is not normal to on-axis reflection 112, so on-axis camera 100 is not in an aligned position in FIG. 2A.

Figure 2B:
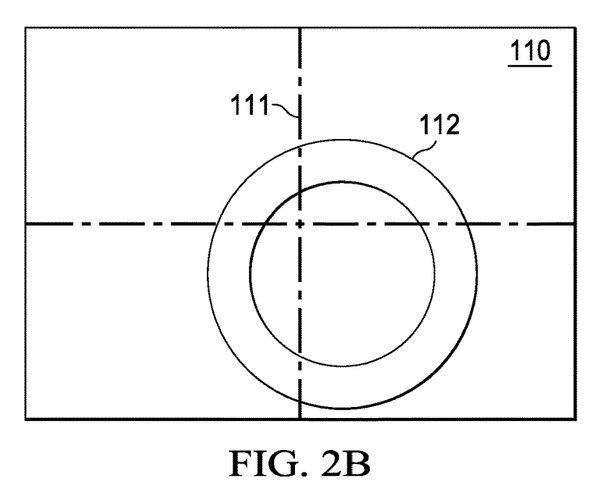
FIG. 2B is a schematic diagram of an on-axis image of an eye captured by the on-axis camera not in an aligned position, as depicted in FIG. 2A.

FIG. 2B depicts an on-axis image 110 captured by an on-axis camera 100 when on-axis camera 100 is not in an aligned position, as shown in FIG. 2A. On-axis camera 100 is not in an aligned position as on-axis reflection 112 is in not the center of on-axis image 110. On-axis reflection 112 is also not in the center of grid 111. To reach an aligned position, the position of all or a portion of ophthalmic system 117 relative to the eye 102 needs to be adjusted at least in the x and y directions.

Figure 2C:
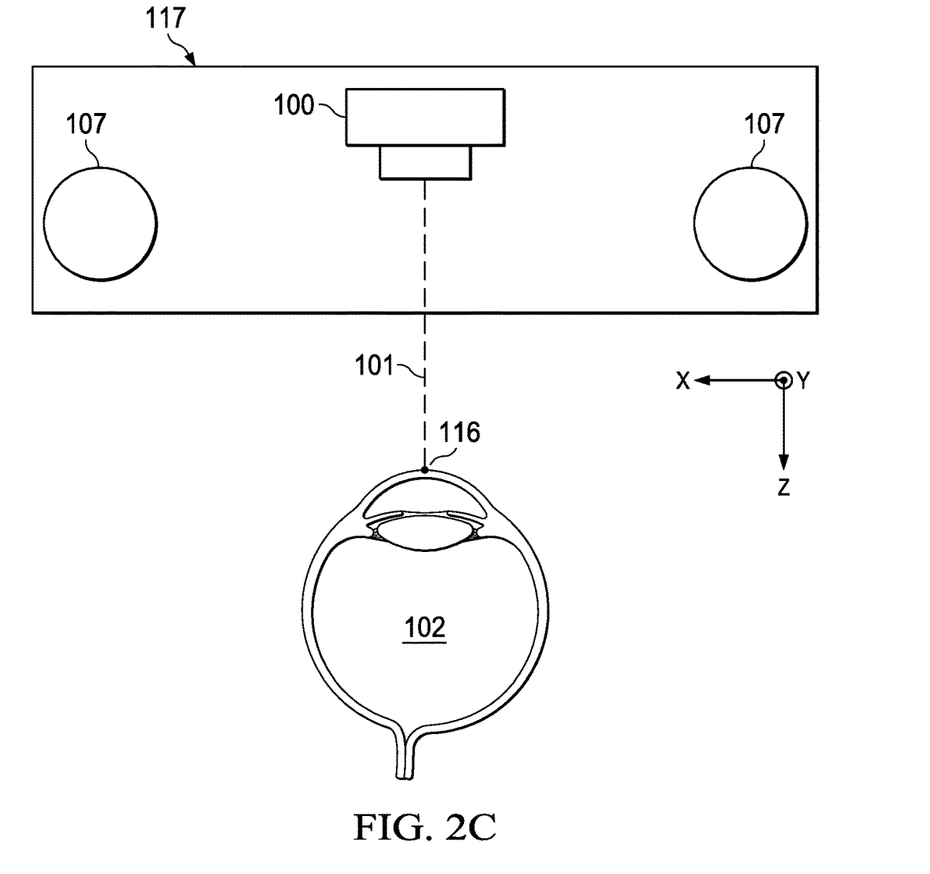
FIG. 2C is a schematic diagram of an ophthalmic system with an on-axis camera and illuminator when on-axis camera is in an aligned position.

FIG. 2C depicts ophthalmic system 117 with an on-axis camera 100 and on-axis illuminator 107 when the on-axis camera 100 is in an aligned position with respect to an eye 102. The position of all or part of the ophthalmic system 117 in FIG. 2C is different in the x and y directions as compared to FIG. 2A. On-axis 101 is normal to the center of the apex 116 of the eye 102. On-axis 101 is normal to on-axis reflection 112, so on-axis camera 100 is in an aligned position in FIG. 2C.

Figure 2D:
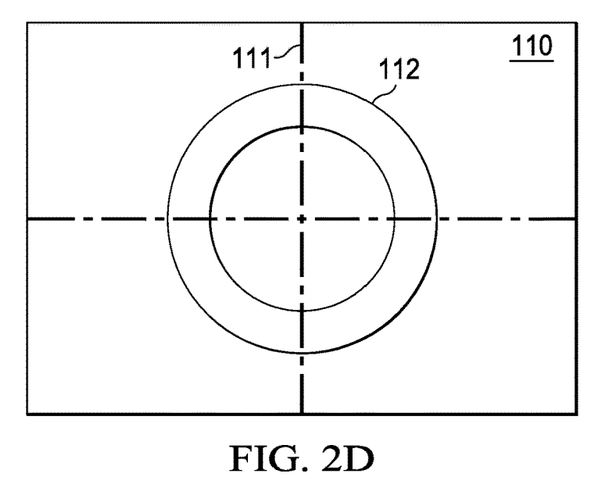
FIG. 2D is a schematic diagram of an on-axis image captured by the on-axis camera in an aligned position, as depicted in FIG. 2C.

FIG. 2D depicts an on-axis image 110 captured by an on-axis camera 100 when on-axis camera 100 is in an aligned position, as shown in FIG. 2C. On-axis camera 100 is in an aligned position as on-axis reflection 112 is in the center of the on-axis image 110. On-axis reflection 112 is also in the center of grid 111.

Figure 3A:
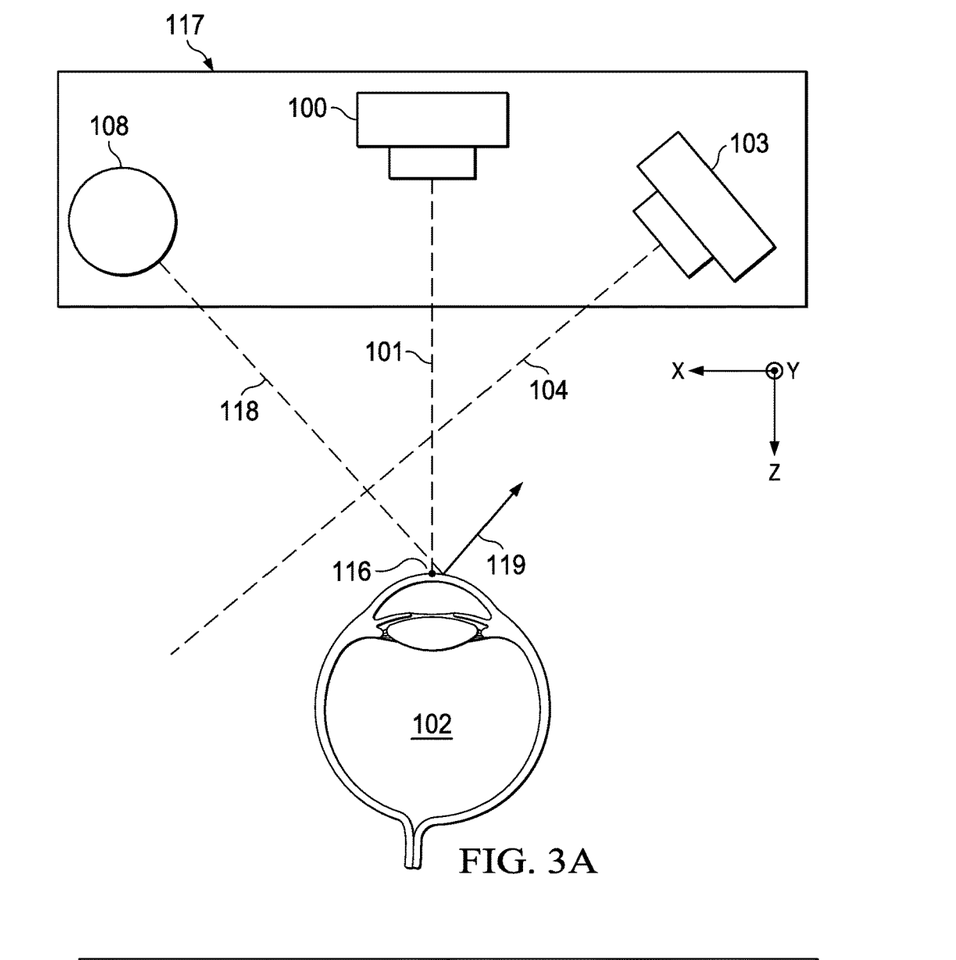
FIG. 3A is a schematic diagram of an ophthalmic system with an on-axis camera, off-axis camera, and off-axis illuminator not in an aligned position with respect to an eye.

FIG. 3A depicts an ophthalmic system 117 with an on-axis camera 100, off-axis camera 103, and off-axis illuminator 108. Ophthalmic system 117 is shown when off-axis camera 103 is not in an aligned position with an eye 102. Off-axis camera 103 is pointed along off-axis 104 generally towards the eye 102. Off-axis 104 intersects on-axis 101 at an off-axis angle γ. Off-axis illuminator 108 emits light toward the eye 102. Light traveling along off-axis incident path 118 is reflected at the eye 102 along the off-axis reflective path 119 to form an off-axis reflection 113. Off-axis 104 is not normal to the center of the apex 116 of the eye 102 or off-axis reflection 113, so off-axis camera 103 is not in an aligned position in FIG. 3A. To reach an aligned position, the position of all or part of the ophthalmic system 117 relative to the eye 102 needs to be adjusted at least in the y direction.

Figure 3B:
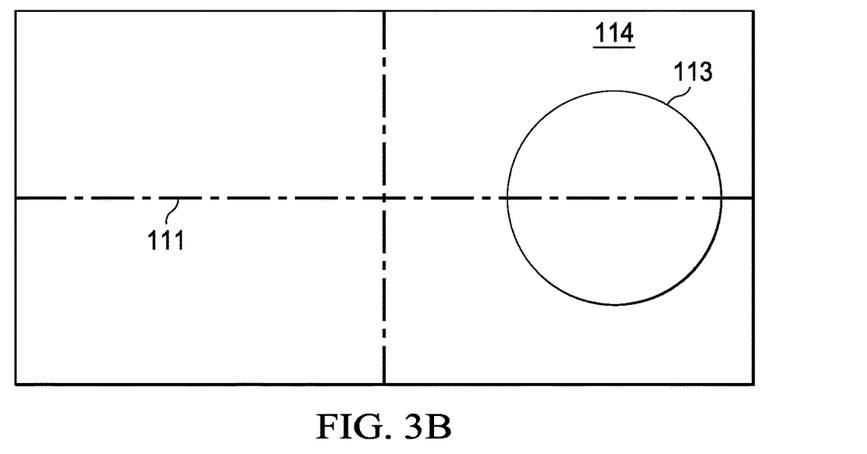
FIG. 3B is a schematic diagram an off-axis image captured by an off-axis camera not in an aligned position with respect to an eye, as illustrated in FIG. 3A.

FIG. 3B depicts an off-axis image 114 captured by an off-axis camera 103 when the off-axis camera 103 is not in an aligned position, as shown in FIG. 3A. The off-axis camera 103 is not in an aligned position as the off-axis reflection 113 is in not the center of the off-axis image 114. The off-axis reflection 113 is also not in the center of grid 115. To reach an aligned position, the position of all or part of the ophthalmic system 117 relative to the eye 102 needs to be adjusted at least in the y direction.

Figure 3C:
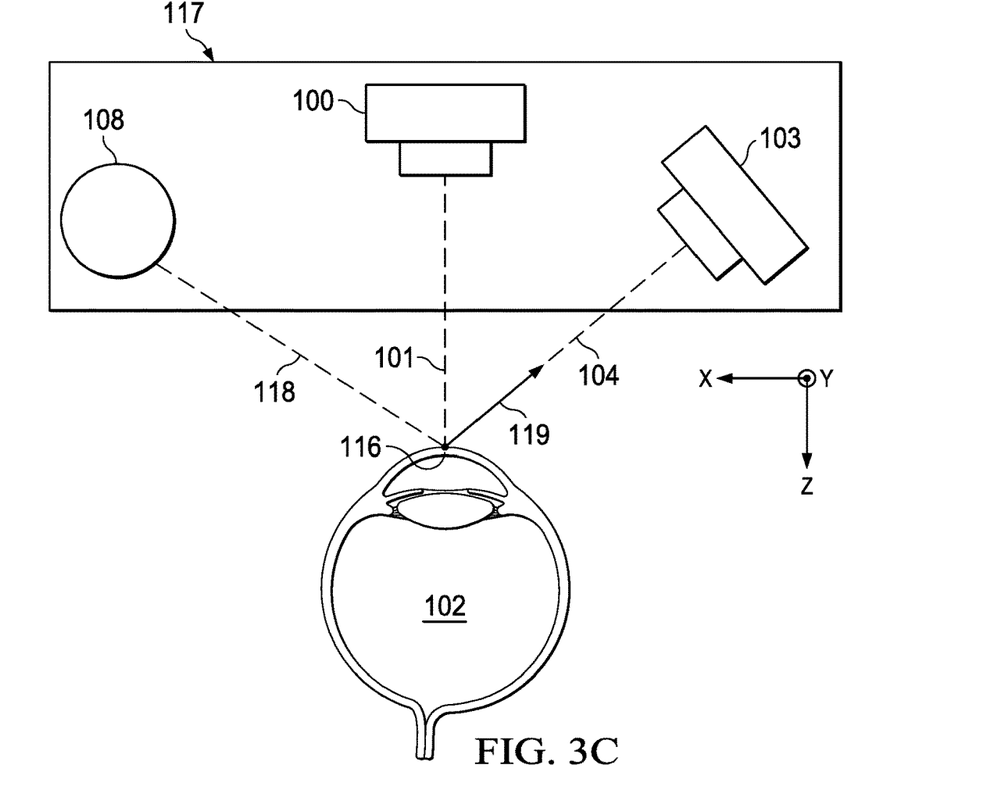
FIG. 3C is a schematic diagram of an ophthalmic system with an on-axis camera, off-axis camera, and off-axis illuminator in an aligned position with respect to an eye.

FIG. 3C depicts an ophthalmic system 117 with an on-axis camera 100, off-axis camera 103, and off-axis illuminator 108. Ophthalmic system 117 is shown when the off-axis camera 103 is in an aligned position with respect to an eye 102. Off-axis 104 is normal to the center of the apex 116 of the eye 102. Off-axis 104 is normal to off-axis reflection 113, so it is in an aligned position in FIG. 3C. Ophthalmic system 117 is aligned since normal 120 at the reflection point 121 is aligned with on-axis 301. Reflection point 121 is determined by light emitted from off-axis illuminator 108. Light travels along off-axis incident path 118 and is reflected to off-axis reflective path 119. Relative to FIG. 3A, the position of the ophthalmic device has been adjusted in the y direction.

Figure 3D:
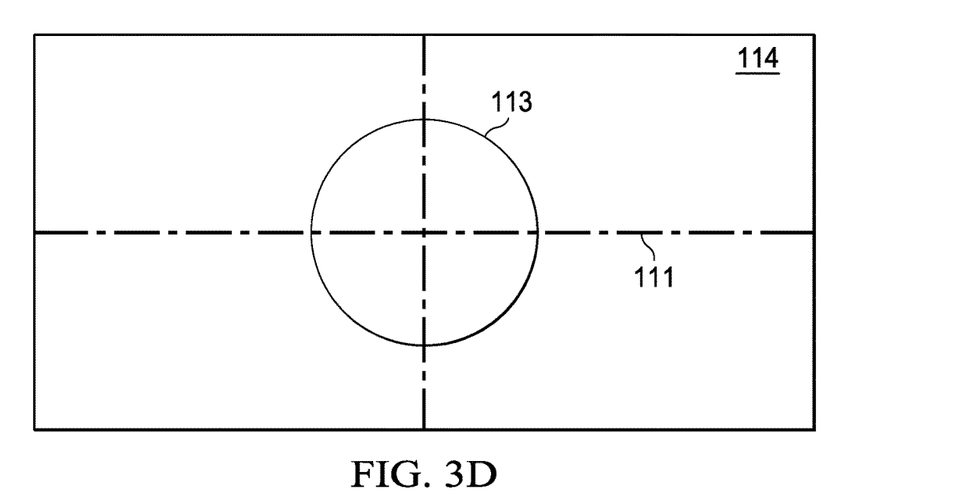
FIG. 3D is a schematic diagram of an off-axis image captured by an off-axis camera is in an aligned position with respect to an eye, as illustrated in FIG. 3C.

FIG. 3D depicts an off-axis image 114 captured by an off-axis camera 103 when the off-axis camera 103 is not in an aligned position, as shown in FIG. 3C. Off-axis camera 103 is in an aligned position as off-axis reflection 113 is in the center of off-axis image 114. Off-axis reflection 113 is in the center of grid 115.

Figure 4:
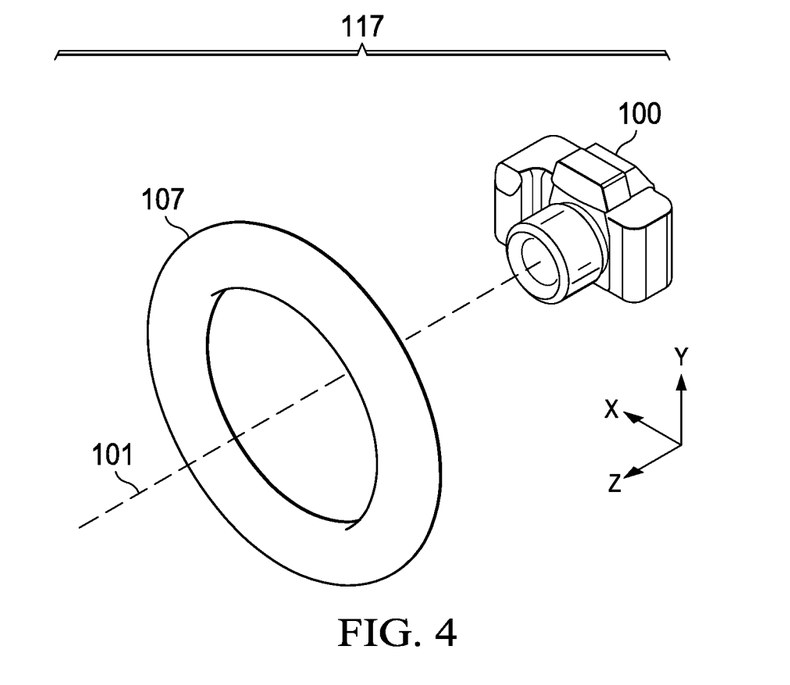
FIG. 4 is a schematic diagram of an ophthalmic system with a camera enclosed by an illuminator.

FIG. 4 depicts an ophthalmic system 117 with on-axis camera 100 enclosed by on-axis illuminator 107. On-axis camera 100 is pointed along on-axis 101. On-axis illuminator 107 may still enclose the on-axis camera 100, whether on-axis camera 100 is in front, aligned, or centered within on-axis illuminator 107 along the y direction. Additionally, on-axis illuminator 107 can be shaped in a may take a variety of shapes for which a center is readily defined, such as a square, rhombus, other regular polygon, or oval, or a dot pattern arranged in such a shape. On-axis illuminator 107 may still enclose on-axis camera 100 if it is shaped to not form an outer boundary with a defined inner area. For example, an on-axis illuminator 107 formed as a line of LEDs may enclose on-axis camera 100 if, e.g., on-axis camera 100 is placed in series with the line of LEDs, with an LED on one side of the camera, and an LED on another. On-axis camera 100 need not be centered within the on-axis illuminator 107 in any direction.

Figure 5A:
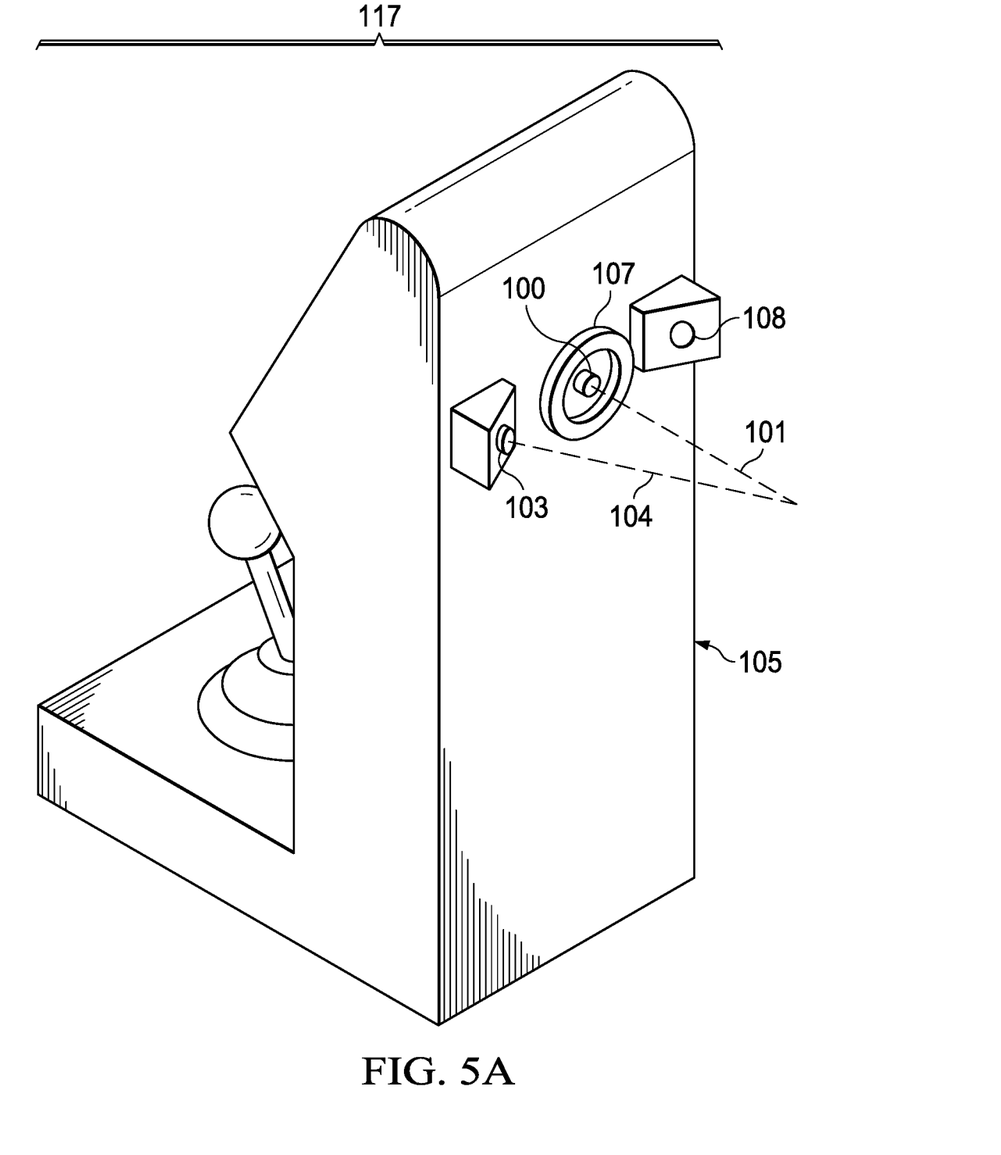
FIG. 5A is a schematic front view an ophthalmic system.
Figure 5B:
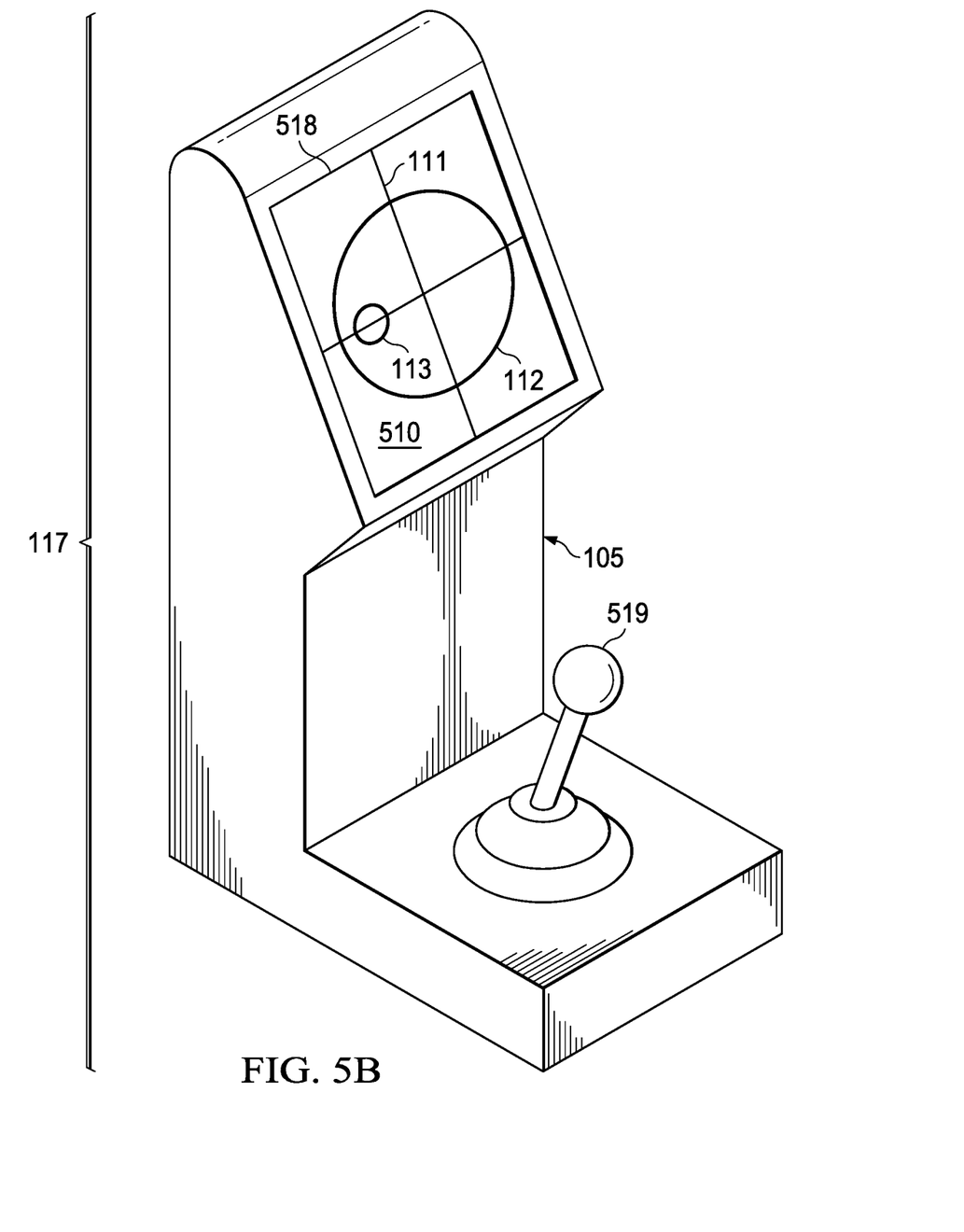
FIG. 5B is a schematic rear view of the ophthalmic system of FIG. 5A with a screen and a control interface.

FIG. 5A is a front view of an ophthalmic system 117. The ophthalmic system 117 may include ophthalmic device 105. Ophthalmic device 105 may include a keratometer, as shown in FIGS. 5A and 5B. Ophthalmic device 105 may include any ophthalmic diagnostic device such as a keratometer, any ophthalmic surgical devices such as a laser, lenses, or any other ophthalmic device. Viewable from the front of ophthalmic system 117, are examples of an on-axis camera 100 pointed along an on-axis 101, an off-axis camera 103 pointed along an off-axis 104, an on-axis illuminator 107, and an off-axis illuminator 108.

FIG. 5B is a rear view of the ophthalmic system 117 shown in FIG. 5A. The ophthalmic system 117 includes a screen 518 and a control interface 519. Screen 518 is shown displaying a processed image 510, depicting an on-axis reflection 112 and an off-axis reflection 113. Screen 518 may be any sort of display, e.g., LED, OLED, LCD, plasma, etc. Screen 518 may be a touch screen. Screen 518 need not be attached to the same physical structure as any of the physical components shown in FIG. 5B and FIG. 5A.

Although processed image 510 in the depicted embodiment only shows one view, it may show multiple views—such as the view from an off-axis camera 103 in addition to a view from on-axis camera 100. Additionally, screen 518 may display a processed image 510 that overlaps images taken from multiple cameras. For example, screen 518 may display an image captured by on-axis camera 100 and superimpose the off-axis reflection of the light emitted an off-axis illuminator received by an off-axis camera 103.

Screen 518 may display augmented reality or graphical representations of the reflected illuminator light to display reflections more clearly or to better communicate the positional information contained therein. Screen 518 may display graphical representations of the on-axis reflection, the off-axis reflection, or both. The graphical representations may depict portions or the entirety of the reflections. Screen 518 may display images of the eye or reflections or graphical representations thereof. Screen 518 may display filtered images, not displaying some data generated by one or more cameras. Screen 518 may also display graphical representations of an eye. Screen 518 may display numerical information such as necessary directional adjustments to achieve alignment. Screen 518 may further display an indication of a pass or fail based on whether the system is aligned in any or all of the spatial directions. A separate light indicator, audible indicator, or physical indicator may indicate a pass or fail indication.

Also depicted in FIG. 5B is a control interface 519. In the depicted embodiment, control interface 519 includes a joystick, but may instead include, e.g., analog buttons, graphical buttons, knobs, foot pedals, etc. Control interface 519 may have virtual components displayed on screen 518. Control interface 519 need not be attached to the same physical structure as any of the physical components shown in FIG. 5B and FIG. 5A. Control interface 519 may receive input from the user in the form of, e.g., a mechanical movement of a joystick or electrical input and may generate a corresponding analog or digital signal. Control interface 519 may have an internal processor or export a generated signal to a motor or a processor. Depending on the signal received, a motor or mechanical structure (e.g., lever) may then adjust a position of all or part of the ophthalmic system in one or more directions.

Figure 6:
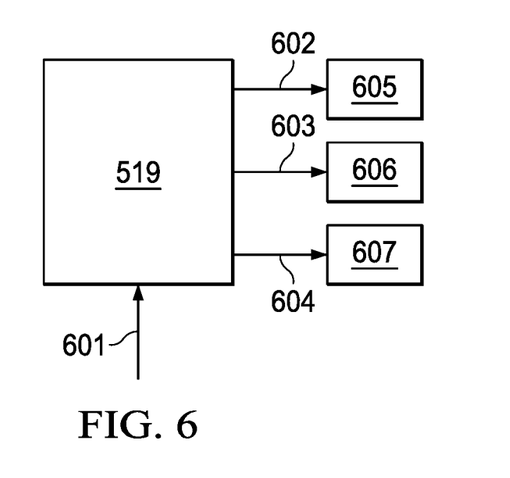
FIG. 6 is a block schematic diagram of a portion of an ophthalmic system with a control interface and motors.

FIG. 6 is a block diagram of a portion of an embodiment of the ophthalmic system 117 of FIGS. 5A and 5B with a control interface 519 and motors 605, 606, and 607. Control interface 519 receives a user input 601 and sends one or more control signals 602, 603, and 604 to one or more motors 605, 606, and 607. User input 601 may be, e.g., a movement by the user of a joystick of the control interface 519. Control interface 519 converts user input 601 to a digital or analog signal and sends a corresponding control signal 602, 603, and 604 to a respective motor 605, 606, and 607.

Each motor 605, 606, or 607 may receive a unique signal or may receive the same signal from the control interface 519 and decode it. Depending on the signal received, a motor 605, 606, or 607 may then adjust a position of all or part of the ophthalmic system 117 in one or more directions, which may correlate with the x-, y- and z-axes described above with respect to eye 102, or in directions that represent movement along two or three of the x-, y-, and z-axes. The user may use the control interface 519 to adjust a position of all or part of the ophthalmic system 117 until it is in an overall aligned position with respect to eye 102. The system may have fewer or more components, such as motors, control signals, and user inputs, than are depicted in FIG. 6.

Figure 7:
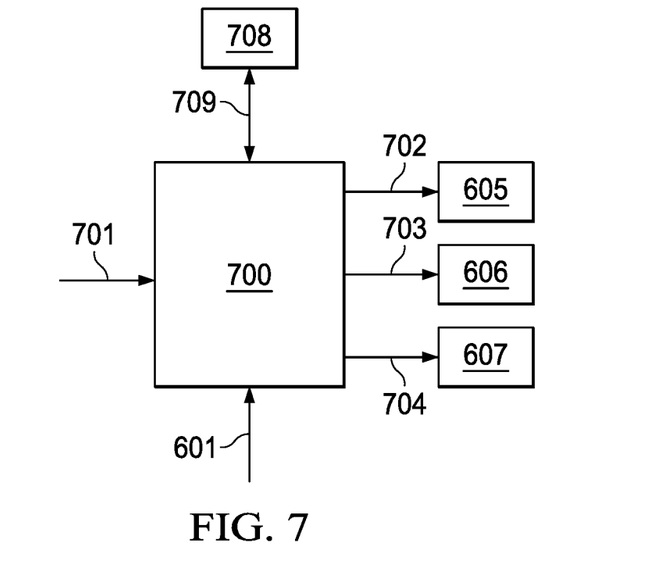
FIG. 7 is a block schematic diagram of a portion of an ophthalmic system with a processor and motors.

FIG. 7 is a block diagram of a portion of an embodiment of the ophthalmic system 117 of FIGS. 5A, 5B, and 6 with a processor 700 and motors 605, 606, and 607. As part of a control interface 519, in addition to a control interface 519, or in lieu thereof, the ophthalmic system 117 may have a processor 700. The processor 700 may receive image data 701 and send one or more instruction signals 702, 703, and 704 to one or more motors 605, 606, and 607. Image data 701 may be data obtained from an on-axis camera, off-axis camera, both, or additional cameras. Image data 701 may include data in any image or video format. Image data may also be pre-processed at an earlier stage. Processor 700 receives image data 701 and may determine, based on image data 701, whether corrective action is needed by, e.g., performing digital image processing.

Processor 700 may compare information contained in the image data 701 to a reference stored in memory 708 to determine if corrective action is needed. User input 610 may be read by the processor 700 and thereafter written to or read from memory 708. Memory 708 and processor 700 may transfer information through memory signal 709.

If corrective action is needed, processor 700 may send one or more instruction signals 702, 703, and 704 to one or more motors 605, 606, and 607. One or more motors 605, 606, and 607 are actuated according to one or more instruction signals 702, 703, and 704 generated by the processor 700. Motors 605, 606, and 607 upon actuation may adjust a position of all or part of the ophthalmic system 117 in one or more directions, which may correlate with the x-, y- and z-axes described above respect to eye 102, or in directions that represent movement along two or three of the x-, y-, and z-axes. Motors 605, 606, and 607 may move part or all of the ophthalmic system, ultimately to an overall aligned position. The actuation and processing may occur automatically upon receiving the image data, in addition to or instead of relying on user input. Accordingly, part or all of the ophthalmic system may be moved based on image data received by cameras.

Additionally, a margin of error may be set by user input 610, may be stored in memory 708, or both. The margin of error can be used to determine whether the difference between the image data and a reference image is within an acceptable range. The margin of error may include one or numerous values containing allowable distances in one or more directions.

The margin of error may include all or any combination of the distances from centers and electronic values described below. For example, the margin of error may include an allowable distance from the center of on-axis 101 to the center of the on-axis reflection 112 in one or more directions, which may correlate with the x-, y- and z-axes described above with respect to eye 102, or in directions that represent distances along two or three of the x-, y-, and z-axes. The margin of error may include an allowable distance from the center of off-axis 104 to the center of the off-axis reflection 113 in one or more directions, which may correlate with the x-, y- and z-axes described above with respect to eye 102, or in directions that represent distances along two or three of the x-, y-, and z-axes. The margin of error may include electronic representations, such as digital or analog values corresponding to an allowable distance from the center of on-axis 101 to the center of the on-axis reflection 112 in one or more directions, which may correlate with the x-, y- and z-axes described above with respect to eye 102, or in directions that represent distances along two or three of the x-, y-, and z-axes. The margin of error may include electronic representations, such as digital or analog values corresponding to an allowable distance from the center of off-axis 104 to the center of the off-axis reflection 113 in one or more directions, which may correlate with the x-, y- and z-axes described above with respect to eye 102, or in directions that represent distances along two or three of the x-, y-, and z-axes. The margin of error can be input via the user input 610, processed by the processor 700, and stored in memory 708. The processor 700 may use a margin of error to determine if corrective action is need. If corrective action is needed, the processor 700 will generate and send one or more instruction signals 702, 703, 704 to actuate one or more motors 605, 606, and 607 to move all or part of the ophthalmic system into an overall aligned position. More or fewer components, such as motors, instruction signals, paths of image data, and user inputs may be used than are illustrated in FIG. 7.

Figure 8:
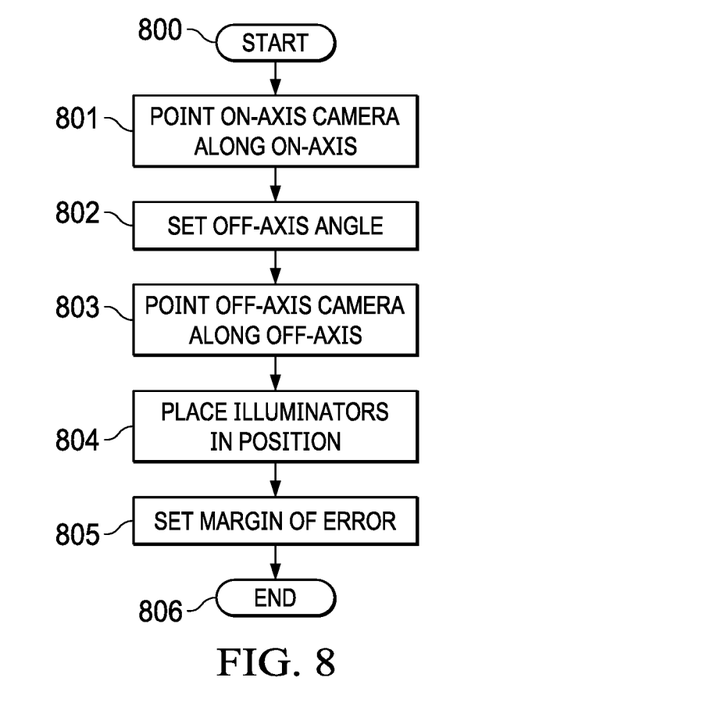
FIG. 8 is a flow chart of a method for arranging components of a system for aligning an ophthalmic device with an eye.

FIG. 8 is a flow chart of a method for arranging components of a system for aligning an ophthalmic device with an eye of a patient. The ophthalmic system may be an ophthalmic system 117 as described in FIGS. 1-7. After starting arranging at step 800, the method includes pointing an on-axis camera along an on-axis at step 801. Pointing at step 801 may set a reference for positioning the other components. Pointing at step 801 may include placing or installing a camera on a system.

The method may include setting an off-axis angle at step 802. The off-axis angle may be set in reference to the on-axis in which the off-axis angle is an acute angle formed at the intersection point of the on-axis and the off-axis. The method may include pointing an off-axis camera along the off-axis at step 803.

The method may include placing one or more illuminators in a position at step 806. An on-axis illuminator may be placed at an on-axis position, where it is able to emit light in a direction that the on-axis camera may capture. An off-axis illuminator may be placed at an off-axis position, where it is able to emit light in a direction that the off-axis camera may capture. Placing illuminators at step 806 may include installing illuminators on a system. An illuminator is placed at a relative position to a camera. The placing illuminators at step 806 may include enclosing an on-axis camera within an illuminator. The placing illuminators at step 806 may include enclosing an off-axis camera within an illuminator.

The method may also include setting a margin of error at step 807. Setting a margin of error at step 807 may include adjusting values in memory or controlling user input.

The method may also include ending the arranging at step 808. The method may include using components or systems as described elsewhere in this disclosure.

Figure 9:
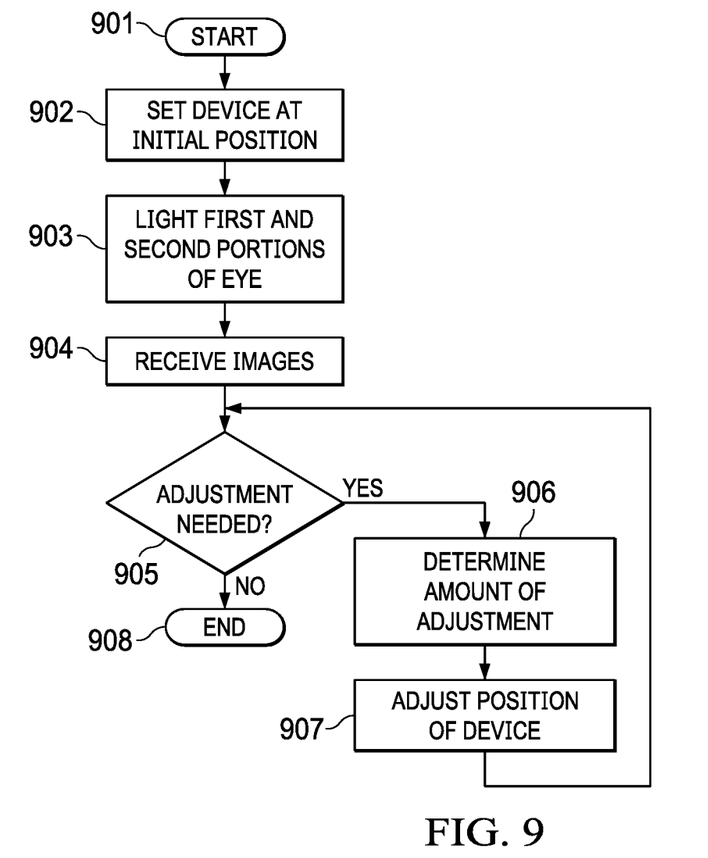
FIG. 9 is a flow chart of a method for aligning a device with an eye.

FIG. 9 is a flow chart of a method for aligning an ophthalmic system with an eye. The ophthalmic system may be ophthalmic system 117 as described with respect to FIGS. 1-7 or aligned using the method of FIG. 8. After starting aligning at step 901, the method may include setting an ophthalmic system at an initial position at step 902.

The method may include lighting a first and second portion of an eye at step 903. The first and second portions may overlap. The first and second portions may be caused by two different illuminators. The method may include receiving images at step 904 with one or more cameras.

The method may include determining if an adjustment is needed at step 905. Determining at step 905 may be done manually by a user, or by a processor, or by a combination of user and processor input. Determining at step 905 answers whether a position of all or part of a system needs to be adjusted relative to an eye in one or more directions, which may correlate with the x-, y- and z-axes described above respect to eye 102, or in directions along two or three of the x-, y-, and z-axes. Determining at step 905 may include sending image data corresponding to one or more images to a processor and generating an instruction signal.

If an adjustment is needed, the method may include determining an amount of adjustment needed at step 906. Determining an amount at step 906 may include determining the amount of adjustment to center all or part of the system, such as the on-axis camera, relative to an eye in x, y, and/or z directions. Determining an amount at step 906 may be done manually by a user, or by a processor, or by a combination of user and processor input. Determining an amount at step 906 may include sending image data of one or more images to a processor and generating an instruction signal. The method may include adjusting a position of all or part of a system relative to an eye at step 907. Adjusting at step 907 may include actuating motors via instruction signals or control signals or mechanically moving all or part of the system.

When an adjustment is no longer needed, or when the on-axis camera 100 and off-axis camera 103 are substantially centered as described above within a margin of error, the method may include ending the aligning at step 908. The method may include using components or systems as described elsewhere in this disclosure.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

The invention claimed is:

1. A system for aligning an ophthalmic device with respect to an eye of a patient, the system comprising:
   an on-axis and an off-axis that intersects the on-axis at an acute off-axis angle; and
   an ophthalmic device comprising:
   an on-axis illuminator operable to emit light that is incident on and reflected by the eye of the patient to form an on-axis reflection having a center;
   an on-axis camera operable to point along the on-axis such that the on-axis camera captures an on-axis image including the on-axis reflection and produces on-axis image data representative of the on-axis image, including the on-axis reflection;
   an off-axis illuminator operable to emit light along an off-axis incident path that is incident on and reflected by the eye along an off-axis reflective path to form an off-axis reflection having a center; and
   an off-axis camera operable to point along the off-axis such that the off-axis camera captures an off-axis image including the off-axis reflection and produces off-axis image data representative of the off-axis image, including the off-axis reflection;
   the ophthalmic device operable to be aligned with respect to the eye of the patient when the on-axis is substantially normal to the center of the on-axis reflection and the off-axis is substantially normal to the center of the off-axis reflection.

2. The system for aligning an ophthalmic device of claim 1,
   wherein the on axis-illuminator encloses the on-axis camera.

3. The system for aligning an ophthalmic device of claim 1, wherein the off-axis illuminator encloses the off-axis camera.

4. The system for aligning an ophthalmic device of claim 2, wherein the on-axis illuminator has a shape with a defined center.

5. The system for aligning an ophthalmic device of claim 1, wherein:
   the system further comprises a processor, the processor operable to receive the on-axis image data and the off-axis image data and produce a pass signal when the ophthalmic device is aligned with respect to the eye of the patient.

6. The system for aligning an ophthalmic device of claim 1, wherein the off-axis angle is between 0° and 90°.

7. The system for aligning an ophthalmic device of claim 1, further comprising:
   a control interface, coupled to receive an input from a user and produce a control signal; and
   a motor coupled to receive the control signal and adjust a position of the ophthalmic device relative to an eye of a patient.

8. The system for aligning an ophthalmic device of claim 1, further comprising:
   a processor operable to receive the on-axis image data and the off-axis image data and send an instruction signal; and
   a motor coupled to receive the instruction signal and adjust a position of the ophthalmic device relative to the eye.

9. The system for aligning an ophthalmic device of claim 1, further comprising a screen coupled to display a processed image, the processed image comprising at least a portion of the on-axis image received by the on-axis camera and at least a portion of the off-axis image received by the off-axis camera.

* * * * *